United States Patent [19]

Pesa et al.

[11] Patent Number: 4,536,597

[45] Date of Patent: Aug. 20, 1985

[54] SELECTIVE HYDROCARBOXYLATION OF PROPYLENE TO ISOBUTYRIC ACID

[75] Inventors: Frederick A. Pesa, Aurora; Thomas A. Haase, University, both of Ohio

[73] Assignee: The Standard Oil Company (Ohio), Cleveland, Ohio

[21] Appl. No.: 108,435

[22] Filed: Dec. 31, 1979

[51] Int. Cl.³ .................... C07C 51/14; C07C 53/124
[52] U.S. Cl. ..................... 562/522; 560/233; 562/599; 568/387; 570/250
[58] Field of Search .......... 562/522; 260/413

[56] References Cited

U.S. PATENT DOCUMENTS

| | | | |
|---|---|---|---|
| 3,437,676 | 4/1969 | Kutepow et al. | 562/522 |
| 3,641,074 | 2/1972 | Fenton | 260/410.9 R |
| 3,661,949 | 5/1973 | Fenton | 260/413 |
| 3,816,490 | 6/1974 | Forster et al. | 260/413 |
| 3,839,378 | 10/1974 | Yamaguchi et al. | 562/522 |
| 3,857,908 | 12/1974 | Wilkinson | 560/233 |
| 3,887,595 | 6/1975 | Nozaki et al. | 562/522 |
| 3,919,272 | 11/1975 | Knifton | 260/410.9 R |
| 3,933,919 | 1/1976 | Wilkinson | 562/522 |
| 3,968,133 | 7/1976 | Knifton | 260/410.9 R |
| 4,245,115 | 1/1981 | Butter | 560/233 |

FOREIGN PATENT DOCUMENTS 2739096 3/1978 Fed. Rep. of Germany.

*Primary Examiner*—Vivian Garner
*Attorney, Agent, or Firm*—T. P. Schur; J. G. Curatolo; L. W. Evans

[57] ABSTRACT

A process for the selective hydrocarboxylation of propylene to produce predominantly isobutyric acid in the liquid phase is provided. The reaction of propylene, carbon monoxide and water wherein a water to propylene ratio is maintained of from about 0.01 to a value less than 1.0 is effected at a temperature of about 75° C. to about 150° C. and at a pressure of about 250 psi to about 5000 psi in the presence of a carboxylic acid solvent and a catalyst comprising a coordinating palladium compound, an organo-arsine and a hydrogen halide.

36 Claims, No Drawings

SELECTIVE HYDROCARBOXYLATION OF PROPYLENE TO ISOBUTYRIC ACID

BACKGROUND OF THE INVENTION

This invention relates to the hydrocarboxylation of olefins to form carboxylic acids. More specifically, this invention relates to the hydrocarboxylation of propylene with CO and H₂O in the liquid phase to produce butyric acid, wherein the isobutyric acid isomer product predominates. The isobutyric acid may then be dehydrogenated to produce methacrylic acid.

Conventionally, hydrocarboxylation of olefins has been intended to produce predominantly the linear, straight-chain or normal (n) isomer of the carboxylic acid desired. U.S. Pat. No. 3,641,074 to Fenton discloses the preparation of normal or straight chained carboxylic acids, esters and anhydrides via the carbonylation of olefins in the presence of a Group VIII noble metal in complex association with a biphyllic ligand. Suitable ligands may include triarylphosphine and triarylarsine among others, and suitable solvents may include hydrocarbons, acids, ketones, ethers and esters, among others.

U.S. Pat. No. 3,816,490 to Forster et al. discloses the production of carboxylic acids by carboxylation of olefins, utilizing a Group VIII metal compound, preferably cobalt, rhodium and iridium together with a phenolic promoter compound. The metal compound may be elemental metal, a simple salt, or an organometallic complex. Acetic acid and propionic acid are disclosed as solvents for the reaction, which yields predominantly normal carboxylic acids when isomeric products are to be prepared.

U.S. Pat. Nos. 3,857,900 and 3,933,919 to Wilkinson disclose hydrogenation, hydroformylation and carbonylation reactions resulting primarily in the formation of linear products when catalysts comprising platinum group metals, ligands containing nitrogen, phosphorus, arsenic or antimony; and a halogen or pseudo-halogen are utilized.

U.S. Pat. Nos. 3,919,272 and 3,968,133 to Knifton disclose the preparation of linear fatty acids and esters from olefins, carbon monoxide and alcohols or water in the presence of ligand-stabilized palladium halide complexes in combination with a halide salt of either tin or germanium. Ligands may include phosphines, and arsines among others. Suitable solvents include aromatic hydrocarbons, ketones, ethers and chlorinated olefins ('272).

The preparation of increased ratios of branched-chain or iso-carboxylic acids to straight-chain acids is described in U.S. Pat. No. 3,661,949 to Fenton. Olefins are hydrocarboxylated in the presence of a biphyllic ligand-stabilized Group VIII noble metal compound catalyst and an iron halide co-catalyst. The ligand may include arsines or phosphines, and suitable solvents include hydrocarbons, ketones, ethers, and acids.

West German Offenlegungsschrift No. 2,739,096 describes the preparation of isobutyric acid esters by the carbonylation of propylene with carbon monoxide and an alcohol in the presence of a palladium salt, a triarylarsine, a halogen acid. Solvents for the reaction include aromatic hydrocarbons, substituted aromatics, chlorinated hydrocarbons, ethers and sulfones. An amount of water larger than about 0.1 mole per mole of propylene is described as being harmful to the carbonylation reaction.

In general the single metal salt catalyst systems are non-selective for the "iso" form of the carboxylic acid products, tending to yield predominantly straight chain products. The catalyst systems described above for use in hydrocarboxylation are often susceptible to deactivation due to the reduction of the Group VIII metal ion particularly palladium, contained therein to the elemental state by the action of the carbon monoxide reactant. These systems may also present difficulties in the separation of the solubilized catalyst from the liquid reaction products. Any catalyst system to be utilized in the hydrocarboxylation reaction must be thermally stable at the temperatures required for the reaction to effectively occur. Other factors which effect the hydrocarboxylation reaction are the solvent used, and the molar ratios of catalyst to stabilizing ligands, to the reactants, and to other components of the system.

SUMMARY OF THE INVENTION

It is therefore an object of the present invention to provide a process for the hydrocarboxylation of propylene in the liquid phase, to produce butyric acid.

It is a further object of the present invention to provide a process for the hydrocarboxylation of propylene in the liquid phase to produce predominantly the isobutyric acid isomer product.

It is a further object of the present invention to provide a process for the hydrocarboxylation of propylene in the liquid phase to produce isobutyric acid utilizing an active palladium catalyst system which is thermally stable, does not readily reduce and is at least partially soluble at the reaction temperatures required.

These and other objects of the present invention, together with the advantages thereof, which shall become apparent from the specification that follows, are accomplished by the invention as hereinafter described and claimed.

In general, the process of the present invention includes the preparation of predominantly isobutyric acid in the liquid phase. A reaction mixture is formed from propylene, carbon monoxide and water in a carboxylic acid-containing solvent in the presence of a soluble, active palladium catalyst system. The reaction mixture is subjected to a temperature of about 75° C. to about 150° C. and a pressure of about 250 psi to about 5000 psi. The catalyst system includes an at least partially soluble palladium salt, an organoarsine compound and a hydrogen halide.

DETAILED DESCRIPTION OF THE INVENTION

The preparation of the iso or branched isomer of butyric acid from propylene, carbon monoxide and water in the liquid phase proceeds according to the following catalyzed reaction.

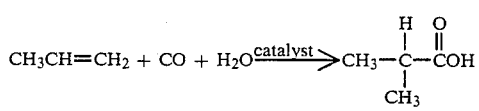

The formation of n-butyric acid, in which all the carbon atoms form a straight chain is to be minimized to the greatest extent possible.

The production of predominantly the "iso" form of butyric acid is made possible by the choice of catalyst system, including stabilizing ligands and complexing acids, and of solvent or reaction media. We have found that other factors which contribute to the unexpected predominance of our desired isomer product include the concentration of water in the reaction medium, the amount of stabilizing ligand with respect to the catalytic metal compound utilized, and the ratio of the amount of propylene fed in the reaction to the amounts of catalyst and solvent present. Still other factors to be considered are reaction temperature, pressure and complexing acid concentration.

The following reaction mechanism has been proposed for the preparation of isobutyric acid from propylene, carbon monoxide and water. This mechanism is merely theoretical and in no way is intended to limit the scope of the present invention, but rather is provided to illustrate the subject reaction.

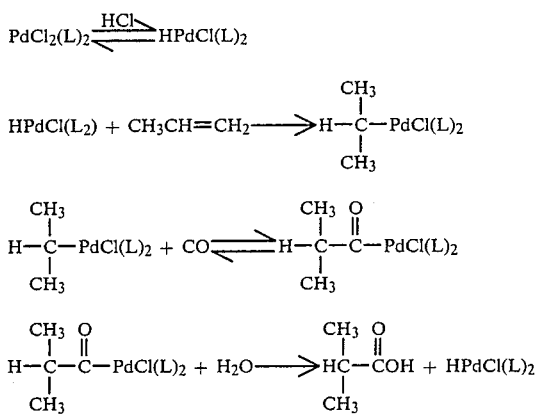

The catalyst system includes a ligand-stabilized, soluble palladium salt compound together with a complexing hydrogen halide acid, preferably hydrochloric acid, optionally with other strong acids, preferably in addition to HCl.

The palladium compound utilized according to the present invention is one which is at least partially soluble and is capable of coordinating carbon monoxide, propylene and water as is demonstrated in the reaction mechanism above. It is therefore preferred that the palladium component of the catalyst be added to the reaction mixture as a palladium salt in the +2 valence state. Suitable palladium salts include Pd(acetate)$_2$, PdCl$_2$, Pd(NO$_3$)$_2$ and the like. The percentage of palladium with respect to the solution utilized should be in the range of about 0.01% to about 10% by weight, preferably in the range of about 0.05 to about 5%. The molar ratio of propylene fed in the reaction to the palladium present, whether in a batch-type reaction or a continuous reaction, is about 10:1 to about 2000:1, preferably about 10:1.

It is preferred that the palladium be maintained in the solubilized state. There is a tendency for the palladium to be reduced to palladium metal and precipitated out of solution, accompanied by the production of acetone, carbon dioxide, molecular hydrogen and propane. The palladium metal, having been reduced in the system, additionally catalyzes the reaction of propylene with hydrogen chloride to form isopropylchloride.

The reduction of palladium (II) to elemental palladium and thus the precipitation of elemental palladium is inhibited in part by the incorporation of stabilizing ligands in the catalyst system. Stabilizing ligands which function effectively as promoters to the subject reaction include arsines of the general formula AsR$_3$ where R is an alkyl or aryl, or an alkoxy or aryloxy group. It is preferred that at least one R be an aryl group or a substituted aryl group which is stable and at least partially unreacted during the course of the reaction. The substituent on the aryl group may be lower alkyl, alkoxide, acid, ester, carbonyl, aromatic, halide, cyanide or the like, where the substituent is in the meta and/or para position. Triarylarsines, particularly triphenylarsine, are preferred stabilizing/promoting ligands. Diarsines and triarsines may also be used, however, rates of reaction are generally considerably slower when using these compounds. The ratio of AsR$_3$/Pd should be at least greater than 2:1 and preferably greater than 20:1 and ratios as high as about 1000:1 may be used. At low AsR$_3$/Pd levels the selectivity of the system is relatively high to isobutyric acid, demonstrating its promotional characteristics. Its stabilizing characteristics are enhanced, however, when the AsR$_3$/Pd ratio is in the preferred range of about 40:1 to about 200:1, at which level the reaction rate and selectivity to isobutyric acid remains high and no palladium reduction (precipitation) is observed.

The catalyst system requires a hydrogen halide which is capable of being coordinated with the palladium metal ion. Hydrogen chloride is preferred and may be supplied to the reaction in aqueous or anhydrous form or as a compound which is capable of releasing HCl under the reaction conditions. HBr and HI can also be used, but the activity of the catalyst system is lower when these are used alone. Mixtures of HCl and HBr or HCl and HI are also used to lend stability to the system. The chloride, bromide, and iodide anions have a greater influence on the reaction, conversion and selectivity than does the proton. The halide component of the hydrogen halide should be present in a ratio of about 5:1 to about 500:1 with respect to the palladium in the system. A preferred ratio of HCl/Pd is from about 45:1 to about 90:1, throughout which range conversion and selectivity to isobutyric acid increase. The HCl/Pd ratio of 90:1 is most preferred. The hydrogen halide component should comprise about 0.1 to 5 wt.% of the total reaction solution.

According to the present invention, the solvent to be utilized in the reaction contains or is a carboxylic acid. Preferred carboxylic acids are those having at least 4 carbon atoms and most preferred are carboxylic acids having from 4 to about 9 carbon atoms. These solvents unexpectedly increase the stability of the catalyst system, the activity of the catalyst with respect to conversion and also the selectivity of the catalyst to isobutyric acid. In addition, carboxylic acids decrease the induction time and increase the reaction rate. These solvents additionally allow easy separation of the product acids from the catalyst solution by distillation. The carboxylic acids may alone comprise the solvent, or may be combined with other organic liquids such as aromatic or substituted aromatic compounds.

When carboxylic acids having at least 4 carbon atoms are utilized, there is substantially no reduction of palladium from the +2 valence state to the precipitated, elemental state. The reduction and precipitation of palladium, however, may also be prevented when using lower carbon atom number carboxylic acids such as acetic acid by controlling the water concentration in the system.

The concentration of water in the reaction medium has been discovered to be critical to maintaining the stability and activity of the catalyst, as well as the selectivity to isobutyric acid. The molar ratio of water to propylene should be maintained within the range of from about 0.01 to a value less than 1.0, preferably about 0.75 or lower, depending upon the manner in which the reaction is conducted.

The reaction of propylene, carbon monoxide and water in the presence of the ligand-stabilized palladium catalyst should be conducted at a temperature in the range of about 75° C. to about 150° C. Preferred temperatures are within the range of about 90° C. to about 125° C. At low temperature, the rate of reaction is unacceptably slow, and at temperatures higher than about 150° C. the catalyst system is unstable.

The reaction should be carried out under a carbon monoxide pressure of about 250 psi to about 5000 psi. Preferred CO pressures are from about 600 psi to about 1200 psi. It has been found that maintaining the reaction at these pressures results in a great increase in the rate of reaction, an increase of selectivity to isobutyric acid, no palladium precipitation and decreased isopropylchloride byproduct production. Maintaining the reaction at high pressure additionally allows a greater throughput to desired products per unit of time.

SPECIFIC EMBODIMENTS OF THE INVENTION

A series of exempletive reactions were carried out in a 300 ml Hastelloy C autoclave in pyrex glass liners. Although the examples were carried out as batch-type reactions to illustrate the present invention, it is intended that the scope of the present invention include continuous feed-type reactions also. Analysis of liquid product was performed on a Hewlett-Packard 5710 A gas chromatograph. Valeric acid was used as the internal standard, and column packing was Polyester FF (trademark of Nishio Industries). Analysis of gases was performed on a Carle III gas analyzer using a Houdry dual column with thermisters as detectors.

The reaction in the examples set forth below were run in the following manner. A pre-weighed solution of palladium acetate, promoter ligand, solvent, water and HCl was placed into the glass liner. Except where noted, generally $5.27 \times 10^{-4}$ mole of Pd(OAc)$_2$ and 28 g of propylene was used. The concentrations of promoter ligand, water and HCl were varied as set forth in the examples and tables below.

After the addition of the above to the autoclave, the autoclave was sealed and mechanical stirring begun. The autoclave was flushed once with an 800 psi charge of carbon monoxide. The propylene was then added to the autoclave from a pre-weighed bomb and the amount of propylene added was measured by weight difference. Carbon monoxide was added to bring the pressure of the autoclave up to 450 psi. The temperature was then increased to the run temperature, and the time was recorded. Carbon monoxide was added to the reactor as needed after it reached run temperature and pressure by the use of a reservoir filled with carbon monoxide. A record of the rate of carbon monoxide addition was made using a pressure transducer attached to a recorder. After the reaction was completed, usually in about 40 minutes, the autoclave was cooled with cold running water. The entire volume of gas vented from the autoclave was collected in a multi-layered gas sampling bag, measured using a wet test meter, and a sample was injected into the Carle III gas analyzer. The liquid effluent was weighed and analyzed as set forth above.

The results of the reaction runs are reported as follows.

$$\% \text{ Conversion} = \frac{\text{Moles of Product Observed} \times 100}{\text{Moles of Propylene Fed}}$$

$$\% \text{ Selectivity} = \frac{\text{Moles of Specific Product} \times 100}{\text{Moles of All Products}}$$

EXAMPLES 1–3

Examples 1, 2 and 3 were run according to the procedure set forth above. The palladium compound employed was palladium acetate, the promoter ligand was triphenyl arsine, and the halogen halide was HCl. Octanoic acid was the solvent. The amount of water used was 9.08 grams, and the Pd(OAc)$_2$/AsR$_3$/HCl ratio was 1/40/90. The amount of propylene fed to the reactions and the other reaction conditions and results are reported in Table I. From Table I it can be seen that as the propylene concentration was increased, the percent conversion decreased greatly, the selectivity to isobutyric acid decreased slightly, even though water was the limiting reactant, and there was a decided increase in the amount of isopropylchloride produced.

EXAMPLES 4–7

The reactions in Examples 4–7 were run according to the procedure set forth above. The molar ratio of water to propylene was 0.75. The palladium compound utilized was palladium acetate, the stabilizing ligand was triphenylarsine, and the hydrogen halide was HCl. The Pd/AsR$_3$ ratio was varied as set forth in Table II. The solvent used as well as reaction conditions and reaction results are listed in Table II. As demonstrated by the results of Table II, although the percentage conversion and percent selectivity to isobutyric acid was high when a low amount of triphenylarsine stabilizing ligand was employed (high Pd/AsR$_3$ ratio) the palladium itself was reduced (precipitated) during the reaction. With a higher amount of triphenylarsine stabilizing ligand present, (a lower Pd/AsR$_3$ ratio) no palladium reduction (precipitation) was observed.

EXAMPLES 8–12

The reactions in Examples 8–12 were run according to the procedure set forth above. The palladium compound utilized was palladium acetate, the promoting ligand was triphenylarsine, and the solvent was octanoic acid. The Pd/AsR$_3$ ratio was 1/40. The complexing acids used as well as reaction conditions and results are included in Table III. As can be seen from the results of Table III, percent conversion and percent selectivity to isobutyric acid is optimized when the HCl/Pd ratio is about 90. Also, other hydrogen halides or other strong acids may be used in combination with HCl to obtain high selectivity to isobutyric acid. Such strong acids include H$_2$SO$_4$, H$_3$PO$_4$ and HBF$_4$.

EXAMPLES 13–16

The reactions in Examples 13–16 were run according to the procedure set forth above. The palladium compound utilized was palladium acetate, the promoter ligand was triphenylarsine, and the hydrogen halide was HCl. The Pd/AsR$_3$/HCl ratio was 1/40/90 and the amount of palladium acetate used was 0.1184 g. The molar ratio of water to propylene was about 0.75. The particular carboxylic acids solvents utilized in these examples are set forth in Table IV together with the other reaction conditions and reaction results. As can be seen from the results in Table IV, the selectivity to isobutyric acid is enhanced when the carboxylic acid solvent has a carbon number greater than or equal to 4, that is the carboxylic acid has at least 4 carbon atoms per molecule. In addition, the rate of reaction increases, and reaction induction time decreases.

EXAMPLES 17-24

The reactions in Example 17-24 were run according to the procedure set forth above. The palladium compound utilized was palladium acetate, the promoting ligand was triphenylarsine, and the hydrogen halide was HCl. The $Pd/AsR_3/HCl$ ratio was 1/40/90. The reaction temperatures used were from about 95° C. to about 110° C., and the pressures were maintained at about 800–900 psi. The solvent and the ratio of water to propylene were varied as set forth in Table V together with other reaction conditions and reaction results. As can be seen from the results in Table V conversion increases as the $H_2O$/propylene ratio approaches one. When the $H_2O$/propylene ratio is very low, less than about 0.05 the by-product isopropylchloride is formed. At an $H_2O$/propylene ratio of about 1, partial palladium reduction (precipitation) begins to occur and at ratios over 1, palladium reduction (precipitation) is more pronounced, resulting in a decrease in selectivity to isobutyric acid. The preferred $H_2O$/propylene ratio is about 0.75 or lower.

EXAMPLES 25-28

The reactions run in Examples 25-28 followed the procedure set forth above. The catalyst system included palladium acetate, triphenylarsine and HCl in a molar ratio of 1/40/90 respectively. The $H_2O$/propylene ratio was 0.75, and all reactions were run in octanoic acid solvent. The reaction conditions and results are set forth in Table VI. As can be seen from the results in Table VI, selectivity to isobutyric acid remains high throughout the temperature range demonstrated. However, the percent conversion is greatest in the temperature range of about 105° C. to about 120° C.

EXAMPLES 29-31

The reactions in Examples 29-31 were run according to the procedure set forth above. The catalyst system consisted of palladium acetate, triphenylarsine and HCl in a molar ratio of 1/40/90 respectively. The $H_2O$/propylene ratio was about 0.75 and the solvent used was octanoic acid. The pressure was held constant in each separate example but was varied from one example to the other. The pressures used, together with other reaction conditions and reaction results are listed in Table VII. As can be seen from the results in Table VII, the selectivity to isobutyric acid remained high throughout the pressure range tested, and the percent conversion increased together with an increase of pressure.

As can be seen from the above examples and Tables, the hydrocarboxylation of propylene with carbon monoxide and water in the presence of a carboxylic acid solvent and a catalyst comprising a palladium salt, an organo-arsine and a hydrogen halide produces a high conversion to butyric acid, particularly with a high selectivity to isobutyric acid generally above about 75%.

The palladium component of the catalyst is maintained in a solubilized state and is prevented from being reduced to an undesired (precipitated) form when an appropriate ratio of propylene to palladium and organoarsine to palladium is employed, as is disclosed above. Conversion and selectivity to isobutyric acid can be optimized by utilizing an appropriate hydrogen halide/palladium ratio as demonstrated above.

The use of a carboxylic acid solvent increases selectivity to isobutyric acid, and this selectivity is optimized when the carboxylic acid utilized contains at least 4 carbon atoms per molecule. In addition, carboxylic acids provide a shorter induction time for the reaction as well as increase the reaction rate as compared to other solvents which have traditionally been utilized for hydrocarboxylation reactions.

The conversion and selectivity to isobutyric acid is optimized when a water to propylene molar ratio less than or equal to one is effected, preferably about 0.75 or lower. A low concentration of water with respect to the palladium component of the catalyst aids in preventing reduction of palladium to the precipitated elemental state.

Thus it should be apparent to those skilled in the art that the subject invention accomplishes the objects set forth above. It is to be understood that the subject invention is not to be limited by the examples set forth therein. These have been provided merely to demonstrate operability, and the selection of specific palladium salts, stabilizer/promoter ligands, hydrogen halides, carboxylic acid solvents and reaction conditions can be determined from the total specification disclosure provide without departing from the spirit of the invention herein disclosed and described, the scope of the invention including modifications and variations that fall within the scope of the attached claims.

TABLE I

The Effect of Propylene Concentration

| Example | Temp. °C. | Pressure (psi) | Time (Min.) | Propylene (g) | % Conv. | % IBA | % NBA | % IP-CL |
|---|---|---|---|---|---|---|---|---|
| 1 | 105 | 840 | 90 | 22.13 | 90.1 | 80.8 | 15.1 | 3.8 |
| 2 | 105 | 840 | 90 | 27.54 | 78.8 | 78.8 | 14.4 | 4.8 |
| 3 | 105 | 840 | 90 | 34.21 | 68.2 | 78.9 | 13.9 | 5.2 |

TABLE II

The Effect of Ligand (Triphenyl Arsine) Concentration

| Example | Catalyst | Temp. | Press. | Time (hrs.) | % Conversion | % IBA | % NBA | Acid Solvent | State of Catalyst |
|---|---|---|---|---|---|---|---|---|---|
| 4 | Pd(OAc)$_2$/AsØ$_3$/HCl 1   40   90 | 110 | 800 | 1½ | 81.5 | 78.4 | 21.6 | Acetic | No Pd reduced |

TABLE II-continued

The Effect of Ligand (Triphenyl Arsine) Concentration

| Example | Catalyst | Temp. | Press. | Time (hrs.) | % Conversion | Selectivity % IBA | Selectivity % NBA | Acid Solvent | State of Catalyst |
|---|---|---|---|---|---|---|---|---|---|
| 5 | Pd(OAc)$_2$/As$\phi_3$/HCl  1  2  90 | 110 | 800 | 1 | 83.0 | 82.0 | 18.0 | Acetic | Pd reduced |
| 6 | Pd(OAc)$_2$/As$\phi_3$/HCl  1  80  90 | 110 | 850 | 1½ | 75.3 | 79.6 | 19.4 | Octanoic | No Pd reduced |
| 7 | Pd(OAc)$_2$/As$\phi_3$/HCl  1  40  90 | 110 | 850 | 1½ | 81.9 | 80.3 | 16.7 | Octanoic | No Pd reduced |

TABLE III

The Effect of HCl Concentration

| Example No. | Temp. (°C.) | Pressure (psi) | Time (Min.) | HCl/Pd Ratio | % Conv. | Selectivity % IBA | Selectivity % NBA | Other Acids |
|---|---|---|---|---|---|---|---|---|
| 8 | 120 | 800–900 | 90 | 45 | 35.8 | 78.8 | 18.0 | — |
| 9 | 120 | 800–900 | 90 | 90 | 81.9 | 80.4 | 16.7 | — |
| 10 | 120 | 800–900 | 90 | 180 | 73.1 | 73.9 | 15.6 | — |
| 11 | 105 | 800 | 90 | 90 | 46.1 | 83.8 | — | Pd/HBr = 1/2 |
| 12 | 105 | 800 | 90 | 90 | 85.0 | 77.2 | — | Pd/HBF$_4$ = 1/90 |

TABLE IV

Effect of Carboxylic Acid Solvent (Carbon Number)

| Example No. | Temp. (°C.) | Pressure (psi) | Acid Solvent | Time (Min) | % Conv. | Selectivity % IBA | Selectivity % NBA |
|---|---|---|---|---|---|---|---|
| 13 | 105 | 840 | Octanoic | 90 | 78.8 | 78.8 | 14.4 |
| 14 | 105 | 880 | Valeric | 90 | ~100 | 82.5 | 14.0 |
| 15 | 105 | 840 | n Butyric | 90 | ~100 | 74.9 | 21.4 |
| 16 | 105 | 880 | Acetic | 90 | 86.2 | 70.5 | 16.7 |

TABLE V

The Effect of H$_2$O Concentration on Conversion and Selectivity

| Example No. | Solvent | H$_2$O/Propylene | Time (min) | % Conv. | % IBA | % NBA | Comments |
|---|---|---|---|---|---|---|---|
| 17 | Acetic Acid | .010 | 160 | 5.17 | 83.8 | 16.2 | i-C$_3$Cl formed |
| 18 | Acetic Acid | 0.26 | 195 | 39.3 | 81.5 | 18.5 | Pd not reduced |
| 19 | Acetic Acid | 0.77 | 90 | 82.7 | 78.4 | 21.6 | Pd not reduced |
| 20 | Acetic Acid | 0.95 | 90 | 80.4 | 76.2 | 23.8 | Partial Pd reduction |
| 21 | Acetic Acid | 2.41 | 90 | 77.4 | 62.1 | 32.9 | Pd reduction |
| 22 | Octanoic Acid | .010 | 90 | 6.1 | 31.5 | 15.3 | i-C$_3$Cl formed |
| 23 | Octanoic Acid | 0.75 | 90 | 81.9 | 80.4 | 16.7 | Pd not reduced |
| 24 | Octanoic Acid | 1.05 | 60 | 90.4 | 81.4 | 16.1 | Partial Pd reduction |

TABLE VI

Effect of Temperature

| Example No. | Temp. °C. | Pressure (psi) | Time (Min.) | % Conv. | Selectivity % IBA | Selectivity % NBA |
|---|---|---|---|---|---|---|
| 25 | 90 | 800–900 | 90 | 22.7 | 80.2 | 14.4 |
| 26 | 105 | 800–900 | 90 | 78.8 | 78.8 | 14.4 |
| 27 | 120 | 800–900 | 90 | 81.9 | 80.4 | 16.7 |
| 28 | 135 | 800–900 | 90 | 68.7 | 83.4 | 12.7 |

TABLE VII

The Effect of CO Pressure

| Example No. | Pressure (psi) | Temp. °C. | Time (min.) | % Conv. | Selectivity % IBA | Selectivity % NBA |
|---|---|---|---|---|---|---|
| 29 | 620 | 105 | 90 | 66.8 | 80.9 | 15.7 |
| 30 | 850 | 105 | 90 | 78.8 | 78.8 | 14.4 |
| 31 | 1150 | 105 | 90 | 81.0 | 83.7 | 14.6 |

We claim:

1. A process for the selective hydrocarboxylation of propylene to produce butyric acid in the liquid phase at a temperature of about 75° C. to about 150° C. and a pressure of about 250 psi to about 5000 psi, wherein the isobutyric acid isomer product predominates, comprising forming a reaction mixture of propylene, carbon monoxide and water in the presence of a carboxylic acid-containing solvent and a catalyst comprising (i) a coordinating palladium compound, (ii) an organoarsine ligand and (iii) a complexing hydrogen halide; and maintaining a water to propylene ratio of from about 0.01 to a value less than 1.0.

2. A process as recited in claim 1 wherein the reaction is carried out at a temperature of about 90° C. to about 125° C.

3. A process as recited in claim 1, wherein the pressure is maintained at about 600 psi to 1200 psi.

4. A process as recited in claims 1 or 3 wherein said pressure is exerted substantially by carbon monoxide.

5. A process as recited in claim 1 wherein said coordinating palladium compound comprises a palladium (II) salt.

6. A process as recited in claim 5 wherein said palladium salt is selected from the group consisting of palladium acetate, PdCl$_2$ and Pd(NO$_3$)$_2$.

7. A process as recited in claim 5, wherein said palladium salt is palladium acetate.

8. A process as recited in claim 5, wherein said palladium salt is PdCl$_2$.

9. A process as recited in claim 5 wherein said palladium salt is Pd(NO$_3$)$_2$.

10. A process as recited in claim 1 wherein said organoarsine is represented by the formula $$As R_3$$

wherein R is alkyl, aryl, alkoxy or aryloxy and at least one R is aryl.

11. A process as recited in claim 10 wherein said organoarsine is a triarylarsine.

12. A process as recited in claim 11 wherein said triarylarsine is triphenylarsine.

13. A process as recited in claim 1 wherein said hydrogen halide is HCl.

14. A process as recited in claim 13 wherein a strong acid in addition to HCl is included as a complexing acid.

15. A process as recited in claim 14 wherein said strong acid is selected from the group consisting of HBr, HI, H$_2$SO$_4$, H$_3$PO$_4$ and HBF$_4$.

16. A process as recited in claims 13, 14 or 15 wherein the molar ratio of HCl to palladium is about 5:1 to about 500:1.

17. A process as recited in claims 13, 14 or 15 wherein the molar ratio of HCl to palladium is about 45:1 to about 90:1.

18. A process as recited in claim 1 wherein said hydrogen halide is one of HBr and HI in addition to HCl.

19. A process as recited in claim 1 wherein said hydrogen halide is selected from the group HCl, HBr and HI.

20. A process as recited in claims 1, 18 or 19 wherein the molar ratio of hydrogen halide to palladium is about 5:1 to about 500:1.

21. A process as recited in claims 1, 18 or 19 wherein the molar ratio of hydrogen halide to palladium is about 45:1 to about 90:1.

22. A process as recited in claim 1 wherein said solvent consists essentially of a carboxylic acid.

23. A process as recited in claim 1 wherein said solvent is a carboxylic acid and at least one additional organic liquid.

24. A process as recited in claim 1 wherein said solvent is a carboxylic acid and at least one additional organic liquid selected from the group consisting of aromatic compounds.

25. A process as recited in claims 1, 22, 23 or 24 wherein said carboxylic acid is acetic acid.

26. A process as recited in claims 1, 22, 23 or 24 wherein said carboxylic acid contains at least 4 carbon atoms per molecule.

27. A process as recited in claims 1, 22, 23 or 24 wherein said carboxylic acid is octanoic acid.

28. A process as recited in claims 1, 22, 23 or 24 wherein said carboxylic acid is butyric acid.

29. A process as recited in claims 1, 22, 23 or 24 wherein said carboxylic acid is valeric acid.

30. A process as recited in claim 1 wherein the molar ratio of propylene to palladium is about 10:1 to about 2000:1.

31. A process as recited in claim 1 wherein the molar ratio of propylene to paladium is about 100:1.

32. A process as recited in claim 1 wherein the molar ratio of organoarsine to palladium is from greater than 2:1 to about 1000:1.

33. A process as recited in claim 1 wherein the molar ratio of organoarsine to palladium is from greater than 20:1 to about 1,000:1.

34. A process as recited in claim 1 wherein the molar ratio of organoarsine to palladium is about 40:1 to about 200:1.

35. A process as recited in claim 1 wherein said water to propylene ratio is about 0.26:1 to about 0.95:1.

36. A process as recited in claim 1 wherein said water to propylene ratio is less than or equal to about 0.75:1.

* * * * *